(12) United States Patent
Blondel et al.

(10) Patent No.: US 9,150,675 B2
(45) Date of Patent: Oct. 6, 2015

(54) COMB POLYMERS WHICH CAN BE USED IN COSMETICS AND DETERGENTS

(71) Applicant: S.P.C.M. SA, Andrezieux Boutheon (FR)

(72) Inventors: Frédéric Blondel, Lezigneux (FR); Antonin Sanna, Saint Etienne (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 251 days.

(21) Appl. No.: 13/839,005

(22) Filed: Mar. 15, 2013

(65) Prior Publication Data

US 2014/0213748 A1    Jul. 31, 2014

(30) Foreign Application Priority Data

Jan. 31, 2013  (FR) ...................................... 13 50823

(51) Int. Cl.
*C08F 36/20* (2006.01)
*C08F 220/56* (2006.01)
(Continued)

(52) U.S. Cl.
CPC ............... *C08F 36/20* (2013.01); *C08F 220/56* (2013.01); *C11D 3/3769* (2013.01); *C11D 3/3773* (2013.01); *C08F 226/02* (2013.01); *C08F 2220/285* (2013.01)

(58) Field of Classification Search
CPC .............................. C08F 220/56; C08F 36/20
USPC ............................................. 526/303.1, 218.1
See application file for complete search history.

(56) References Cited

U.S. PATENT DOCUMENTS 5,278,269 A * 1/1994 Mita et al. ................... 526/303.1
6,069,216 A * 5/2000 Iwasaki et al. ................ 526/258
2010/0292116 A1* 11/2010 Uchiyama et al. ............ 510/122

FOREIGN PATENT DOCUMENTS

AU    2004200189 B2    2/2004
EP    0372546 A2    6/1990
(Continued)

OTHER PUBLICATIONS

French Search Report for French Patent Application No. 1350823 (Oct. 11, 2013).
(Continued)

*Primary Examiner* — Ling Choi
*Assistant Examiner* — Chun-Cheng Wang
(74) *Attorney, Agent, or Firm* — Heslin Rothenberg Farley & Mesiti, P.C.

(57) ABSTRACT

A water-soluble copolymer comprising, by mass relative to the total mass of the copolymer:
  1 to 40% of at least one cationic monomer;
  59.99 to 98% of at least one nonionic monomer;
  0.01 to 10% of at least one monomer of formula (I);

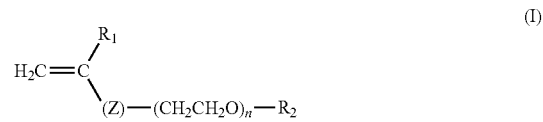

in which:
  $R_1$ is a hydrogen atom or a methyl radical;
  Z is a divalent group —C(=O)—O—, or —C(=O)—NH—;
  n is an integer between 2 and 200;
  $R_2$ is a hydrogen atom or a carbon-containing radical which is saturated or unsaturated, optionally aromatic, linear, branched or cyclic, comprising 1 to 30 carbon atoms, and from 0 to 4 heteroatoms chosen from the group comprising O, N and S;
the copolymer having a cationic charge density between 0.05 and 3 meq/g.

20 Claims, 1 Drawing Sheet

(51) Int. Cl.
*C11D 3/37* (2006.01)
*C08F 226/02* (2006.01)
*C08F 220/28* (2006.01)

(56) References Cited

FOREIGN PATENT DOCUMENTS

| | | |
|---|---|---|
| EP | 1765893 A2 | 3/2007 |
| EP | 1769011 A2 | 4/2007 |
| JP | 07285831 A | 10/1995 |
| JP | 2000302649 A | 10/2000 |
| JP | 2002322219 A | 11/2002 |
| JP | 2003055164 A | 2/2003 |
| WO | 2006013268 A2 | 2/2006 |
| WO | 2006013271 A1 | 2/2006 |

OTHER PUBLICATIONS

Database WPI, Week 200957, Thomson Scientific, London, GB; AN 2009-L64412, XP002714566, & CN 101 475 691 (Jul. 8, 2009).
Goddard, E. Desmond. "Polymer/Surfactant Interaction in Applied Systems." *Principles of Polymer Science and Technology in Cosmetics and Personal Care*, 1999, Chapter 5, Marcel Dekker, Inc., U.S.

\* cited by examiner

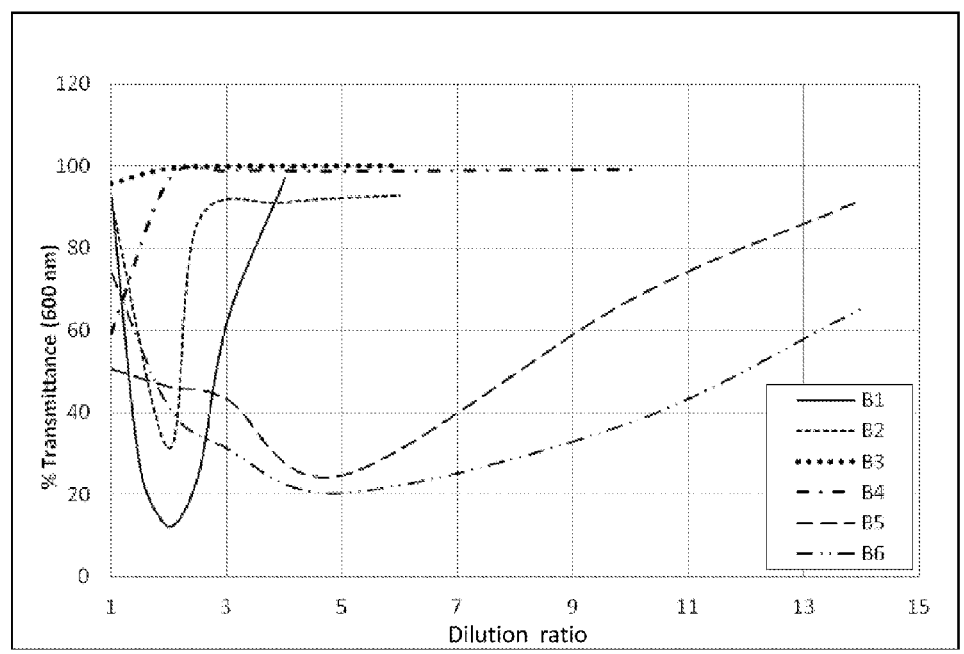

US 9,150,675 B2

COMB POLYMERS WHICH CAN BE USED IN COSMETICS AND DETERGENTS

CROSS REFERENCE TO RELATED APPLICATIONS

This application is a U.S. national application filed under 35 U.S.C. §111(a), and claims priority to French priority document FR 1350823, filed on Jan. 31, 2013, the entire disclosure of which is hereby incorporated herein by reference.

The present invention relates to the technical field of polymers with a "comb" structure, and more specifically cationic polymers with a comb structure having hydrophilic pendant chains. These polymers with a comb structure find applications in particular in the fields of cosmetics and detergents.

A polymer with a comb structure has a structure similar to that of a comb. In other words, it comprises a principal chain to which side chains are attached which may be different in nature and of variable length. For example, these side chains may have hydrophilic and/or hydrophobic properties. They can be made of ethylene oxide unit, propylene oxide unit and alkyl type unit, and the like, with lengths of 2 to 500 units and preferably 5 to 200 units in the case of a pendant chain of the poly(ethylene oxide) type.

Polymers with a comb structure of the prior art comprise in particular polymers based on polyethylene glycol (meth)acrylate (PEGMA) units and on cationic units.

The document EP372546 describes copolymers based on PEGMA, monomers of the $C_1$-$C_8$ alkyl (meth)acrylamide type, and optionally cationic monomers.

The document JP2002-322219 describes polymers containing PEGMA units in association with hydrophobic monomers based on polypropylene glycol (PPO) or poly(tetramethylene oxide), and cationic monomers.

The document JP2003-055164 describes cross-linked polymers containing units of the PEGMA type; however, these polymers are cross-linked, which makes their synthesis more complicated.

The document JP2000-302649 also describes a hair composition comprising a polymer based on cationic monomers having quaternary amine groups, monomers with a polyether group, in particular of the PEG (polyethylene glycol) or PPO type, and optionally hydrophobic monomers (for example stearyl methacrylate).

The document JP07-285831 describes hair compositions containing a polymer based on PEGMA-type monomers combined with ionic, cationic or amphoteric monomers, and additional monomers of the $C_1$-$_{24}$ alkyl (meth)acrylate type, which are mainly hydrophobic.

The documents EP1769011 and EP1765893 describe polymers mainly consisting of cationic units and PEGMA units.

The document WO2006/013268 describes polymers comprising at least one monomer of the PEG (meth)acrylate type combined with a monomer having a cationic (cationic, amphoteric or cationic and anionic) character.

The document AU 2004 200 189 describes a polymer which may comprise a monomer of the PEG acrylate type combined with a monomer which may be cationic but which does not comprise a quaternary ammonium functional group.

The document WO2006/013271 describes a cosmetic composition comprising a polymer containing a monomer of the PEG methacrylate type combined with a monomer not comprising a quaternary ammonium functional group.

As already stated, the fields of application of polymers with a comb structure are in particular cosmetics and detergents. They may therefore be present as a conditioner, a foaming agent or an agent for promoting deposition in cosmetic compositions of body and hair products, or in detergents.

In aqueous solution, the interactions between a cationic polyelectrolyte and species of opposite charge may result in the precipitation of a complex. This complex (or coacervate) corresponds to the adsorption of anionic species on the polyelectrolyte. In some cases, the complex may be solubilized by adding an excess of anionic species.

It is known that these coacervates have advantageous properties of conditioning and of promoting the deposition of an active agent (*Principles of polymer science and technology in cosmetics and personal care—Polymer/surfactant interaction in applied systems* E.D Doddard).

However, the polymers commonly used have a number of disadvantages.

For example, polymers of natural origin such as guar gums or hydroxycellulose do not naturally possess cationic charges. Consequently, an additional step is therefore necessary in order to make them cationic. Now, the distribution of charges on the polymer during this step is random, which does not ensure the availability of the charge which may be present either on the main chain or on the side chains.

The use of these polymers is also a disadvantage. Because of their natural origin, their dissolution takes long and is tedious.

Moreover, natural polymers, and in particular derivatives of guar, are also useful in other applications, such as the food industry or textiles, but also the exploitation of unconventional gas and oil resources. This creates pressure on the availability of these products and causes pricing problems.

The problem which the applicant proposes to solve is to provide cationic polymers which can form coacervates during their dilution in the presence of anionic species, while being free of the constraints of the prior art.

The applicant has developed polymers which make it possible in particular to optimize the formation of these coacervates.

The present invention thus relates to polymers which, once incorporated into a cosmetic or detergent composition, facilitate the formation of coacervates resulting from the ionic attraction between two compounds of opposite charge.

The polymers thus have a better interaction with the compounds which may be present in formulations such as surfactants, other polymers and active ingredients. These polymers also have a better affinity with the hair and the skin for cosmetics or surfaces for detergents.

The subject of the present invention is therefore a water-soluble copolymer with ethylene units, comprising, as a percentage by mass relative to the total mass of the copolymer:
  1 to 40% of at least one cationic monomer whose cationicity comes exclusively from one or more quaternary ammonium functional groups;
  59.99 to 98% of at least one nonionic monomer;
  0.01 to 10% of at least one monomer of formula (I);

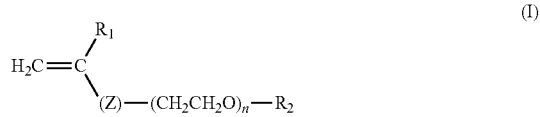

in which:
  $R_1$ is a hydrogen atom or a methyl radical;
  Z is a functional group chosen from the group comprising a covalent bond, an oxygen atom, the divalent group —CH$_2$—O—, —C(=O)—O—, and —(=O)—NH—;

n is an integer between 2 and 200;

R$_2$ is a hydrogen atom or a carbon-containing radical which is saturated or unsaturated, optionally aromatic, linear, branched or cyclic, comprising 1 to 30 carbon atoms, comprising from 0 to 4 heteroatoms chosen from the group comprising O, N and S.

Advantageously, n is between 7 and 45.

Advantageously, the water-soluble copolymer with ethylene units comprises, as a percentage by mass relative to the total mass of the copolymer:

1 to 30% of at least one cationic monomer whose cationicity comes exclusively from one or more quaternary ammonium functional groups;

60 to 90% of at least one nonionic monomer;

0.01 to 10% of at least one monomer of formula (I).

The term "water-soluble" denotes a copolymer which may be dissolved in an aqueous solution, in an amount of at least 50 g/L at 25° C., without leaving insoluble particles.

In addition, according to one essential characteristic of the invention, the cationicity of the copolymer is advantageously between 0.05 and 3 meq/g, preferably between 0.05 and 1.8 meq/g.

The cationicity or cationic charge density corresponds to the cationic equivalent number per unit of mass.

In other words, in the case where the copolymer comprises a cationic monomer A, and a noncationic monomer B, it is determined according to the following formula:

$$\text{cationicity(meq/g)} = (1000 \times \% A)/(\% A \times Mw_A + \% B \times Mw_B)$$

in which:

% A represents the molar percentage of the cationic monomer A;

% B represents the molar percentage of the noncationic monomer B;

Mw$_A$ represents the molar mass of the cationic monomer A;

Mw$_B$ represents the molar mass of the noncationic monomer B.

The cationic charge density therefore depends on the proportions of monomers and their respective molar masses. Consequently, at equivalent monomer ratio, two polymers do not necessarily have the same cationic charge density considering the molar mass of each of the monomers.

According to a preferred embodiment, in the monomer of formula (I), R$_2$ is either a hydrogen atom; a benzyl radical; a phenyl radical optionally substituted with at least one C$_1$-C$_{12}$ alkyl; a linear or branched C$_1$-C$_{30}$ alkyl radical, optionally comprising at least one cyclic group, and optionally at least one aromatic group, in particular as C$_1$-C$_{22}$, or even as C$_2$-C$_{16}$, optionally comprising 1 to 4 heteroatoms chosen from O, N and S. Mention may be made in particular of the methyl, ethyl, propyl, benzyl, ethylhexyl, lauryl, stearyl and behenyl radicals.

The monomers of formula (I) which are most particularly preferred may be chosen from the group comprising poly(ethylene glycol) (meth)acrylates, methyl-poly(ethylene glycol) (meth)acrylates, poly(ethylene glycol) vinyl alkylenes, poly(ethylene glycol) oxyvinyl butylenes. Preferably, they are monomers whose molar mass is advantageously between 80 and 8000 g/mol, more advantageously between 300 and 2000 g/mol.

Among the preferred monomers of formula (I), there may be mentioned:

poly(ethylene glycol) (meth)acrylate in which R$_1$=H or CH$_3$; Z=C(=O)—O—; R$_2$=H; with n=2 to 200;

methyl-poly(ethylene glycol) (meth)acrylate, also called methoxy-poly(ethylene glycol) (meth)acrylate, in which R$_1$=H or CH$_3$; Z=C(=O)—O—; and R$_2$=CH$_3$; with n=2 to 200;

alkyl-poly(ethylene glycol) (meth)acrylates in which R$_1$=H or CH$_3$; Z=C(=O)—O—; and R$_2$=C$_1$-C$_{30}$ alkyl; with n=2 to 200;

phenyl-poly(ethylene glycol) (meth)acrylates, also called poly(ethylene glycol) phenyl ether (meth)acrylate, in which R$_1$=H or CH$_3$; Z=C(=O)—O—; and R$_2$=phenyl; with n=2 to 200;

poly(ethylene glycol) vinyl alkylenes, in which R$_1$=H or CH$_3$; Z=—CH2-O—; R$_2$=H or C$_1$-C$_{30}$ alkyl; with n=2 to 200;

poly(ethylene glycol) oxyvinyl butylenes, in which R$_1$=H or CH$_3$; Z=covalent bond; R$_2$=H or C$_1$-C$_{30}$ alkyl; with n=2 to 200.

Among the commercial monomers, there may be mentioned:

polyethylene glycol 8000 or 4000 methacrylates marketed by Monomer & Polymer Dajac laboratories;

poly(ethylene glycol) methacrylates, with a molar mass of 5000 g/mol, available from EVONIK under the trade name VISIOMER®;

hydroxy-poly(ethylene glycol) methacrylates marketed by CLARIANT under the trade name POLYGLYKOL® MA;

poly(ethylene glycol) vinyl alkylenes marketed by Liaoning oxiranchem company under the trade name OXAB;

poly(ethylene glycol) oxyvinyl butylenes marketed by Zhejiang Huangma Chemical Industry group under the trade name HMXB-45.

The cationic monomer(s) which may be used in the context of the invention may be chosen in particular from monomers of the acrylamide, acrylic, vinyl, allyl or maleic type having a quaternary ammonium functional group. Mention may be made, in particular and without limitation, of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC) and methacrylamidopropyltrimethylammonium chloride (MAPTAC).

The nonionic monomer(s) which may be used in the context of the invention may be chosen in particular from the group comprising water-soluble vinyl monomers. Preferred monomers belonging to this class are, for example, acrylamide, methacrylamide, N-isopropylacrylamide, N,N-dimethylacrylamide and N-methylolacrylamide. Also, use may be made of N-vinylformamide, N-vinylacetamide, N-vinylpyridine and N-vinylpyrrolidone, acryloylmorpholine (ACMO) and diacetone acrylamide. A preferred nonionic monomer is acrylamide.

According to some embodiments, in addition to the above monomers, the water-soluble copolymer(s) may also comprise one or more hydrophobic monomers chosen in particular from monomers of the acrylamide, acrylic, vinyl, allyl or maleic type having a pendant hydrophobic functional group preferably chosen from acrylamide derivatives such as N-alkylacrylamides, for example, diacetone acrylamide, N-tert-butylacrylamide, octylacrylamide, and N,N-dialkylacrylamides such as N,N-dihexylacrylamide and acrylic acid derivatives such as alkyl acrylates and methacrylates. Also, use may be made of derivatives of vinyl monomers such as N-vinylformamide, N-vinylacetamide, N-vinylpyridine, and N-vinylimidazole.

The copolymer may in addition be structured by at least one structuring agent which may be chosen from the group comprising polyethylenically unsaturated monomers (having at least two unsaturated functional groups), such as for example vinyl, allyl, acrylic and epoxy functional groups and mention may be made for example of methylene bisacrylamide (MBA), triallyamine, polyethylene glycol diacrylate, or alternatively using macro initiators such as polyperoxides, polyazo compounds and polytransfer agents such as polymer-captan polymers.

According to the invention, and in an advantageous manner, the polymer is not crosslinked. It may be linear or structured, that is to say branched, star-shaped (in the form of a star) or comb-shaped (in the form of a comb).

Whatever of its structure, the polymer which is the subject of the invention has hydrophilic pendant chains derived from the monomer of formula (I).

In general, the polymers of the invention do not require the development of a specific polymerization process. Indeed, they may be obtained according to all the polymerization techniques well known to a person skilled in the art. These may be in particular solution polymerization; gel polymerization; precipitation polymerization; (aqueous or inverse) emulsion polymerization; suspension polymerization; or micellar polymerization.

The polymer may be provided in liquid or solid form when its preparation includes a drying step such as spray-drying, drying on a drum or alternatively microwave drying.

The term "anionic species" is understood to mean all the macromolecular elements having an anionic character which are commonly present in cosmetic or detergent type formulations and the like.

Consequently, the present invention also relates to the use of the copolymer described above in a cosmetic or detergent formulation.

Without limitation, these ionic species may be:
(i) Anionic surfactants among which there may be mentioned, alone or mixed, salts (in particular alkali metal salts, in particular sodium salts, ammonium salts, amino salts, salts of amino alcohols or magnesium salts) of the following compounds: alkyl sulfates, alkyl ether sulfates, alkyl amido ether sulfates, alkyl aryl polyether sulfates, monoglyceride sulfates, alkyl sulfonates, alkyl phosphates, alkyl amide sulfonates, alkyl aryl sulfonates, alpha-olefin sulfonates, paraffin sulfonates, alkyl sulfosuccinates, alkyl ether sulfosuccinates, alkyl amide sulfosuccinates, alkyl sulfosuccinamates; alkyl sulfoacetates, alkyl ether phosphates, acyl sarcosinates, acyl isethionates, N-acyltaurates. The alkyl or acyl radical of all these various compounds preferably comprises from 8 to 24 carbon atoms, while the aryl radical preferably denotes a phenyl or benzyl group.

Mention may also be made of the salts of fatty acids such as the salts of oleic, ricinoleic, palmitic and stearic acids, the salts of acids of copra oil or of hydrogenated copra oil; the salts of acyl lactylates in which the acyl radical comprises 8 to 20 carbon atoms; the salts of alkyl D-galactoside uronic acids as well as the salts of polyoxyalkylenated ($C_6$-$C_{24}$)alkyl ether carboxylic acids, the salts of polyoxyalkylenated ($C_6$-$C_{24}$) alkyl aryl ether carboxylic acids, the salts of polyoxyalkylenated ($C_6$-$C_{24}$)alkyl amidoether carboxylic acids, in particular those comprising from 2 to 50 ethylene oxide groups; and mixtures thereof.
(ii) Anionic polyelectrolytes comprising at least one monomer having an acrylic, vinyl, maleic, fumaric or allyl functionality and containing a carboxy, phosphonate or sulfonate group, or another group having an anionic charge. There may in particular be: acrylic acid, methacrylic acid, itaconic acid, crotonic acid, maleic acid, fumaric acid, and monomers of the strong acid type having for example a functional group of the sulfonic acid or phosphonic acid type such as 2-acrylamido-2-methylpropanesulfonic acid, vinylsulfonic acid, vinylphosphonic acid, allylsulfonic acid, allylphosphonic acid.
(iii) Natural polymers having an anionic character which may be chosen from the group comprising polysaccharides such as cellulose, starch, guar gum, guar gum hemicellulose, gum arabic, glucomannan, carob gum, pullulan, curdlan, xanthan gum, gellan gum, carrageenan gum, dextran gum, tragacanth gum, welan gum, rhamsan gum, hyaluronic acid, inulin, pectin, lignin, chitin, alginate, agar agar or derivatives thereof.

The invention and the advantages resulting therefrom will emerge more clearly from the following figures and examples given so as to illustrate the invention and without limitation.

FIGS.

FIG. 1 represents a graph corresponding to the transmittance of solutions containing a cationic polymer and anionic species, as a function of the dilution of said solution.

EXAMPLES OF IMPLEMENTATION OF THE INVENTION

A/ Preparation of the Copolymers
Preparation of polymer A1: polymer according to the invention.

The following are loaded in a reactor equipped with a mechanical stirring system, a condenser, a thermometer and a nitrogen inlet:
- 19.7 g of a 64% dimethyldiallylammonium chloride solution
- 62.7 g of a 50% acrylamide solution
- 2.1 g of mPEG 2000 MA (Visiomer mPEG 2005 MA, Evonik). It is a methoxypolyethylene glycol methacrylate whose molar mass is 2000 g/mol.
- 365.5 g of water The reaction medium is deoxygenated with a nitrogen stream, and heated at 75° C.

Separately, an initiator solution is prepared by introducing 0.45 g of 2,2'-azobis(2-amidinopropane) dihydrochloride (V50, Wako) in 20 g of water.

When the temperature of the medium has reached 75° C., continuous feeding of the initiator solution is started. The solution is added for 120 minutes and then the medium is kept at 75° C. for 120 additional minutes in order to complete the polymerization.

The mixture is allowed to return to room temperature and then the pH is adjusted to between 4 and 6 using an aqueous NaOH or citric acid solution at 50% by mass.

The product obtained is a liquid solution whose polymer concentration is 10% by mass relative to the mass of the solution. The solution has a viscosity of 3000 cps (Brookfield LVT, module 3, 30 rpm). The polymer A1 has a cationic charge density of 1.7 meq/g.

Preparation of polymer A2: branched polymer according to the invention.

Polymer A2 is prepared using the experimental conditions described during the preparation of A1, but adding 88 mg of polyethylene glycol 600 diacrylate during loading of the reactor.

The product obtained is a liquid solution whose polymer concentration is 10% by mass relative to the mass of the solution. The solution has a viscosity of 14000 cps (Brookfield LVT, module 4, 30 rpm).

The polymer A2 has a branched structure. The polymer A2 has a cationic charge density of 1.7 meq/g.

Preparation of polymer A3: modification of the composition of the polymer (counter example).

Polymer A3 is prepared using the experimental conditions described during the preparation of A1 but loading the following quantities into the reactor:
- 17.7 g of a 64% dimethyldiallylammonium chloride solution
- 56.1 g of a 50% acrylamide solution
- 11.2 g de mPEG 2000 MA (Visiomer mPEG 2005 MA, Evonik). It is a methoxypolyethylene glycol methacrylate whose molar mass is 2000 g/mol.
- 365 g of water The product obtained is a liquid solution whose polymer concentration is 10% by mass relative to the mass of the solution. The solution has a viscosity of 800 cps (Brookfield LVT, module 3, 30 rpm). The polymer A3 has a cationic charge density of 1.5 meq/g.

B/Study of the Formation of a Coacervate Between the Polymers and Anionic Polyelectrolytes Method of Characterization The objective is to demonstrate the capacity of a polymer to form a coacervate with anionic species during dilution.

The formulations B1-B6 of table 1 are prepared with the polymers A1-A3 and prior art polymers.

The use of the cationic guars (formulations B5 and B6) is long and difficult. Their dissolution in water requires vigorous stirring for a period of about 20 minutes (technical documents Rhodia: Recommended procedure for formulating cationic Jaguar, Jaguar Excel data sheet and Jaguar C13S data sheet).

The polymers prepared according to examples A1, A2 and A3 have the advantage of being perfectly solubilized in water after a few seconds of stirring only.

The formulations B1 to B6 are then diluted in water in several ratios. The transmittance at 600 nm of each of the solutions thus obtained is measured with the aid of a spectrophotometer.

The formation of a coacervate during the dilution is shown by a reduction in the transmittance (appearance of cloudiness) (tables 2 and 3; FIG. 1).

Results:

The dilutions of the formulations B1 to B6 lead to the following measurements of transmittance:

TABLE 2

Measured transmittance for dilute solutions, based on formulations B1-B3.

| B1 | | B2 | | B3 | |
| --- | --- | --- | --- | --- | --- |
| Dilution ratio | % transmittance (600 nm) | Dilution ratio | % transmittance (600 nm) | Dilution ratio | % transmittance (600 nm) |
| 1 | 92.4 | 1 | 91 | 1 | 95.7 |
| 1.5 | 26.1 | 2 | 31.2 | 2 | 99.4 |
| 2 | 12.3 | 2.5 | 86.4 | 3 | 99.8 |
| 2.5 | 24.7 | 4 | 91.2 | 6 | 100 |
| 3 | 62 | 6 | 92.9 | | |
| 4 | 96.9 | | | | |

TABLE 1

Formulations B1-B6 (percentages by weight).

| | Formula | | | | | |
| --- | --- | --- | --- | --- | --- | --- |
| | B1 | B2 | B3 | B4 | B5 | B6 |
| Water | qs 100% | qs 100% | qs 100% | qs 100% | qs 100% | qs 100% |
| Polymer A1 | 1% | | | | | |
| Polymer A2 | | 1% | | | | |
| Polymer A3 | | | 1% | | | |
| Polyquaternium 7 (Flocare C107) | | | | 1% | | |
| Guar hydroxypropyltrimonium chloride (Jaguar C13S) | | | | | 1% | |
| Guar hydroxypropyltrimonium chloride (Jaguar Excel) | | | | | | 1% |
| Cocamidopropyl betaine | 3% | 3% | 3% | 3% | 3% | 3% |
| Sodium Lauryl Ether Sulfate | 8% | 8% | 8% | 8% | 8% | 8% |
| NaCl | 1% | 1% | 1% | 1% | 1% | 1% |

TABLE 3

Measured transmittance for dilute solutions, based on formulations B4-B6.

| B4 | | B5 | | B6 | |
|---|---|---|---|---|---|
| Dilution ratio | % transmittance (600 nm) | Dilution ratio | % transmittance (600 nm) | Dilution ratio | % transmittance (600 nm) |
| 1 | 59.3 | 1 | 50.6 | 1 | 74 |
| 2 | 96.7 | 2 | 46.3 | 2 | 41.3 |
| 3 | 98.9 | 3 | 43.3 | 3 | 31.3 |
| 5 | 98.8 | 5 | 24.8 | 5 | 20.4 |
| 10 | 99.2 | 10 | 67.4 | 10 | 37.6 |
|  |  | 14 | 91.6 | 14 | 65.3 |

The dilutions of formulations B1 to B6 are illustrated by FIG. 1.

Conclusion:

When they are formulated with anionic species and then diluted, the polymers of the invention allow the formation of coacervates.

The transmittance of formulations B1-B6 is compared to the reference transmittance of water (100%).

The invention claimed is:

1. A water-soluble copolymer comprising, by mass relative to the total mass of the copolymer, units derived from:
   1 to 40% of at least one cationic monomer whose cationicity comes exclusively from one or more quaternary ammonium functional groups;
   59.99 to 98% of at least one nonionic monomer;
   0.01 to 10% of at least one monomer of formula (I):

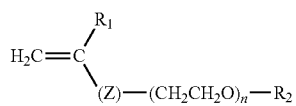

wherein said monomer of formula (I) is selected from the group consisting of:
   poly(ethylene glycol) (meth)acrylate in which $R_1$=H or $CH_3$; $Z$=C(=O)—O—; $R_2$=H; n=2 to 200;
   methyl-poly(ethylene glycol) (meth)acrylate, in which $R_1$=H or $CH_3$; $Z$=C(=O)—O—; $R_2$=$CH_3$; n=2 to 200;
   alkyl-poly(ethylene glycol) (meth)acrylates in which $R_1$=H or $CH_3$; $Z$=C(=O)—O—; $R_2$=$C_1$-$C_{30}$ alkyl; n=2 to 200;
   phenyl-poly(ethylene glycol) (meth)acrylates, in which $R_1$=H or $CH_3$; $Z$=C(=O)—O—; $R_2$=phenyl; n=2 to 200;
   poly(ethylene glycol) vinyl alkylenes, in which $R_1$=H or $CH_3$; $Z$=—$CH_2$—O—; $R_2$=H or $C_1$-$C_{30}$ alkyl; with n=2 to 200; and
   poly(ethylene glycol) oxyvinyl butylenes, in which $R_1$=H or $CH_3$; $Z$=covalent bond; $R_2$=H or $C_1$-$C_{30}$ alkyl; with n=2 to 200;
   the copolymer having a cationic charge density between 0.05 and 3 meq/g.

2. The copolymer as claimed in claim 1, wherein the copolymer comprises by mass relative to the total mass of the copolymer, units derived from:
   1 to 30% of at least one cationic monomer whose cationicity comes exclusively from one or more quaternary ammonium functional groups;
   60 to 90% of at least one nonionic monomer;
   0.01 to 10% of at least one monomer of formula (I).

3. The copolymer as claimed in claim 1, wherein the copolymer has a cationic charge density between 0.05 and 1.8 meq/g.

4. The copolymer as claimed in claim 1, wherein the monomer of formula (I) is selected from the group consisting of poly(ethylene glycol) (meth)acrylates and methyl-poly(ethylene glycol) (meth)acrylates, having a molar mass between 80 and 8000 g/mol.

5. The copolymer as claimed in claim 1, wherein the cationic monomer is selected from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC), and methacrylamidopropyltrimethylammonium chloride (MAPTAC).

6. The copolymer as claimed in claim 1, wherein the nonionic monomer is selected from the group consisting of acrylamide, methacrylamide, N-isopropylacrylamide, N,N-dimethylacrylamide, N-methylolacrylamide, N-vinylformamide, N-vinylacetamide, N-vinylpyridine, N-vinylpyrrolidone, acryloylmorpholine (ACMO) and diacetone acrylamide.

7. The copolymer according to claim 1, wherein n is an integer between 7 and 45.

8. A cosmetic or detergent formulation comprising the copolymer according to claim 1.

9. The copolymer as claimed in claim 2, wherein the monomer of formula (I) is selected from the group consisting of:
   poly(ethylene glycol) (meth)acrylate in which $R_1$=H or $CH_3$; $Z$=C(=O)—O—; $R_2$=H; n is an integer between 7 and 45;
   methyl-poly(ethylene glycol) (meth)acrylate, in which $R_1$=H or $CH_3$; $Z$=C(=O)—O—; $R_2$=$CH_3$; n is an integer between 7 and 45;
   alkyl-poly(ethylene glycol) (meth)acrylates in which $R_1$=H or $CH_3$; $Z$=C(=O)—O—; $R_2$=$C_1$-$C_{30}$ alkyl; n is an integer between 7 and 45;
   phenyl-poly(ethylene glycol) (meth)acrylates, in which $R_1$=H or $CH_3$; $Z$=C(=O)—O—; $R_2$=phenyl; n is an integer between 7 and 45;
   poly(ethylene glycol) vinyl alkylenes, in which $R_1$=H or $CH_3$; $Z$=—CH2—O—; $R_2$=H or $C_1$-$C_{30}$ alkyl; n is an integer between 7 and 45; and
   poly(ethylene glycol) oxyvinyl butylenes, in which $R_1$=H or $CH_3$; $Z$=covalent bond; $R_2$=H or $C_1$-$C_{30}$ alkyl; n is an integer between 7 and 45.

10. The copolymer as claimed in claim 9, wherein the monomer of formula (I) is selected from the group consisting of poly(ethylene glycol) (meth)acrylates and methyl-poly(ethylene glycol) (meth)acrylates, having a molar mass between 80 and 8000 g/mol.

11. The copolymer as claimed in claim 9, wherein the cationic monomer is selected from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC), and methacrylamidopropyltrimethylammonium chloride (MAPTAC).

12. The copolymer as claimed in claim 9, wherein the nonionic monomer is selected from the group consisting of acrylamide, methacrylamide, N-isopropylacrylamide, N,N-dimethylacrylamide, N-methylolacrylamide, N-vinylformamide, N-vinylacetamide, N-vinylpyridine, N-vinylpyrrolidone, acryloylmorpholine (ACMO) and diacetone acrylamide.

13. The copolymer as claimed in claim 3, wherein the monomer of formula (I) is selected from the group consisting of:
- poly(ethylene glycol) (meth)acrylate in which $R_1$=H or $CH_3$; Z=C(=O)—O—; $R_2$=H; n is an integer between 7 and 45;
- methyl-poly(ethylene glycol) (meth)acrylate, in which $R_1$=H or $CH_3$; Z=C(=O)—O—; $R_2$=$CH_3$; n is an integer between 7 and 45;
- alkyl-poly(ethylene glycol) (meth)acrylates in which $R_1$=H or $CH_3$; Z=C(=O)—O—; $R_2$=$C_1$-$C_{30}$ alkyl; n is an integer between 7 and 45;
- phenyl-poly(ethylene glycol) (meth)acrylates, in which $R_1$=H or $CH_3$; Z=C(=O)—O—; $R_2$=phenyl; n is an integer between 7 and 45;
- poly(ethylene glycol) vinyl alkylenes, in which $R_1$=H or $CH_3$; Z=—CH2—O—; $R_2$=H or $C_1$-$C_{30}$ alkyl; n is an integer between 7 and 45; and
- poly(ethylene glycol) oxyvinyl butylenes, in which $R_1$=H or $CH_3$; Z=covalent bond; $R_2$=H or $C_1$-$C_{30}$ alkyl; n is an integer between 7 and 45.

14. The copolymer as claimed in claim 13, wherein the monomer of formula (I) is selected from the group consisting of poly(ethylene glycol) (meth)acrylates and methyl-poly(ethylene glycol) (meth)acrylates, having a molar mass between 80 and 8000 g/mol.

15. The copolymer as claimed in claim 13, wherein the cationic monomer is selected from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC), and methacrylamidopropyltrimethylammonium chloride (MAPTAC).

16. The copolymer as claimed in claim 13, wherein the nonionic monomer is selected from the group consisting of acrylamide, methacrylamide, N-isopropylacrylamide, N,N-dimethylacrylamide, N-methylolacrylamide, N-vinylformamide, N-vinylacetamide, N-vinylpyridine, N-vinylpyrrolidone, acryloylmorpholine (ACMO) and diacetone acrylamide.

17. The copolymer as claimed in claim 2, wherein the cationic monomer is selected from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC), and methacrylamidopropyltrimethylammonium chloride (MAPTAC).

18. The copolymer as claimed in claim 3, wherein the cationic monomer is selected from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC), and methacrylamidopropyltrimethylammonium chloride (MAPTAC).

19. The copolymer as claimed in claim 2, wherein the nonionic monomer is selected from the group consisting of acrylamide, methacrylamide, N-isopropylacrylamide, N,N-dimethylacrylamide, N-methylolacrylamide, N-vinylformamide, N-vinylacetamide, N-vinylpyridine, N-vinylpyrrolidone, acryloylmorpholine (ACMO) and diacetone acrylamide.

20. The copolymer as claimed in claim 1, wherein the copolymer is not cross-linked.

* * * * *